United States Patent [19]

Cornell

[11] Patent Number: 4,885,161

[45] Date of Patent: Dec. 5, 1989

[54] WOUND DRESSINGS IN GELLED PASTE FORM

[75] Inventor: John Cornell, West Chester, Pa.

[73] Assignee: Medi-Tech International Corporation, Brooklyn, N.Y.

[21] Appl. No.: 294,907

[22] Filed: Jan. 6, 1989

Related U.S. Application Data

[63] Continuation-in-part of Ser. No. 24,268, Mar. 11, 1987, abandoned.

[51] Int. Cl.$^4$ ............................................. A61K 31/74
[52] U.S. Cl. ..................................... 424/78; 424/447; 424/484; 424/487; 128/156
[58] Field of Search ............................... 424/447–448, 424/484–488, 78; 128/156

[56] References Cited

U.S. PATENT DOCUMENTS

| | | | |
|---|---|---|---|
| 3,849,238 | 11/1974 | Gould et al. | 161/159 |
| 4,248,685 | 2/1981 | Beede et al. | 204/159.22 |
| 4,554,317 | 11/1985 | Behar et al. | 525/28 |
| 4,556,056 | 12/1985 | Fischer et al. | 128/156 |
| 4,675,009 | 6/1987 | Hymes et al. | 604/304 |

*Primary Examiner*—Nancy A. B. Swisher
*Attorney, Agent, or Firm*—Bernard Malina

[57] ABSTRACT

A gelled paste composition is provided for dressing of skin wounds. The dressing comprises:
 (i) a non-cross-linked, nonionic polyacrylamide or polymethacrylamide;
 (ii) a cross-linked salt of polyacrylic or polymethacrylic acid; and
 (iii) water. The components are present in the critical ratios of (i) to (ii) of from about 1:25 to 1:15; the ratio of (i) plus (ii) to (iii) being from about 10:1 to 1:3. Glycerine is also a desirable component and, when present, will be found in a ratio of water to glycerine ranging from 5:1 to 1:0.7.

14 Claims, No Drawings

WOUND DRESSINGS IN GELLED PASTE FORM

This is a continuation-in-part of application Ser. No. 024,268 filed Nov. 11, 1987 now abandoned.

FIELD OF THE INVENTION

The invention concerns novel skin dressings which aid in the healing of wounds.

BACKGROUND OF THE INVENTION

Burns, ulcerations, severe abrasions, skin transplants and similar poorly healing wounds affecting relatively large areas of skin are particularly vulnerable to infection. Artificial skins have been developed as bandages to temporarily protectively cover these wounds. These bandages must promote biofixation, control bacterial growth, supply moisture and prevent evaporation.

U.S. Pat. No. 3,849,238 (Gould et al.) discloses artificial skin comprising a water-containing hydrophilic polymer sponge layer and a thinner hydrophobic polymer layer. Illustrative of the hydrophilic polymers are hydroxyalkyl acrylates or methacrylates, acrylamides, and derivatives thereof. The hydrophobic component may be alkoxyalkyl acrylates or methacrylates, vinylacetate polymers, elastomeric silicone or polymerized olefins such as polyisoprene, polybutadiene or polyethylene.

U.S. Pat. No. 4,248,685 (Beede et al.) reports aqueous hydrocolloidal dispersions of random interpolymers having bacteriostatic properties. These interpolymers can initially be prepared as gels. Gelled material can then be cast into a self-supporting, transparent, conformable film wound dressing. The interpolymers are derived from the polymerization of a monomer mixture comprising 10–90% alpha, beta-olefinically unsaturated carboxylic acid esters with 90–10% alpha, beta-olefinically unsaturated amides capable of being dispersed in water. A difunctional monomer such as $N,N^1$-methylene bisacrylamide must also be present to crosslink the polymer mixture.

U.S. Pat. No. 4,554,317 (Behar et al.) describes a synthetic hydrophilic membrane for use as a wound covering. The membrane is prepared by graft polymerization of a hydrophilic monomer with a polyurethane substrate. Included among the hydrophilic monomers are acrylamides, hydroxyalkyl acrylates and hydroxyalkyl methacrylates. Gamma radiation and x-rays are suggested as suitable for initiating the graft polymerization.

U.S. Pat. No. 4,556,056 (Fischer et al.) discloses transparent gels in sheet or strip form for use as fluid bandages. These sheets are produced by dissolving a monomer and a gellable polysaccharide in water and therein initiating free-radical polymerization of the monomer.

A review of the foregoing patents reveals that the compositions are intended to be either powder compositions, membranes or cast sheet type products. These formulations do not take into consideration the special problems of gelled pastes deliverable from tubes. These pastes must be sufficiently gelled to avoid being of soft, limp, flowable consistency. Pastes which run will not adequately adhere to a wound. On the other hand, there is the danger of over gellation. Pastes which are too thick are difficult to extrude from tube containers. There is also the aesthetic problem when dealing with too loose or too thick paste formulations.

Water-absorption rates have also not readily been controllable by the compositions of the prior art. It is important that the rate of fluid uptake be neither too rapid nor too slow. A modest controlled rate of moisture absorption must be exhibited by such products.

Consequently, it is an object of this invention to provide a wound dressing in a gelled paste form.

Another object of this invention is to provide a dressing which is neither too limp nor too thick for dispensing through laminated tubes and which adheres to the wound area.

A further object of this invention is to provide a paste which has a moderate, controlled rate of fluid absorption.

SUMMARY OF THE INVENTION

These and other objectives have been met by an extrudable gelled paste composition for dressing skin wounds comprising:

(i) a non-cross-linked polymer selected from a polyacrylamide or polymethacrylamide;

(ii) a cross-linked salt of a polycarboxylic acid selected from polyacrylic or polymethacrylic acids; and (iii) water; wherein the ratio of (i) to (ii) ranges from about 1:2.5 to about 1:10, and the ratio of (iii) to the sum of (i) and (ii) ranges from about 10:1 to 1:3.

DETAILED DESCRIPTION OF THE INVENTION

The wound dressing of the present invention is a granulated gel in the form of a paste. This inert hydrogel formulation is composed of a sterile solution of a polymeric structurant and incorporating a special moisture absorbent. The granulated gel provides a moist environment to aid in the healing process. Granules of the paste form a gel on the wound; these granules will then continuously soften in the presence of moisture. They have the ability to absorb wound exudate, thereby acting as a wound cleansing agent. Exudate diffuses into the gel which assists in the removal of contaminants from the wound. Gentle swabbing of the wound with a saline solution easily removes the gel in preparation for a fresh application of gel.

The compositions of the present invention are particularly effective in encouraging granulation and epithelization over chronic ulcers, especially *ulcers cruris* and *decubitis ulcers*.

An important component of the composition is the polymeric structurant. The present invention utilizes a non-cross-linked essentially nonionic polyacrylamide or polymethacrylamide homopolymer. These polymers are commercially available from the American Cyanamide Company. Especially preferred is Gelamide 250 which is a homopolymer of acrylamide having a molecular weight of approximately five to six million. Low molecular weight polymers have been found to be unsuitable as structurants. Thus, it is important that the polyacrylamide or polymethacrylamide have a molecular weight within the range of one to ten million; preferably the range should be from about five to eight million. When the molecular weight is too low the gelled paste becomes soft, limp, extremely flexible, and separates into small pieces; the paste flows as a lumpy fluid.

The amount of polyacrylamide or polymethacrylamide will generally range from about 0.1 to about 20% by weight of the composition; preferably from about 0.5 to 10%; optimally from about 0.8 to about 2%.

The moisture absorbing agent is a second crucial element of the compositions subject of the present invention. For purposes of moisture absorption there must be present a salt of a polyacrylic or polymethacrylic acid which must be highly cross-linked. Polyacrylic or polymethacrylic acids which are lightly or non-cross-linked were found to dissolve in water very rapidly which resulted in a weak gel. Illustrative of a suitable polyacrylic acid is the commercially available material Water-Lock J-550 sold by the Grain Processing Corporation. Water-Lock J-550 is a superabsorbent polymer which is available in the form of swellable beads. The swellable bead form is preferred for purposes of the present invention.

Appropriate counterions for polyacrylic or polymethacrylic acid are sodium, potassium, lithium, ammonium, substituted ammonium, and cation mixtures thereof. These polymeric water absorbent salts may be present in amounts from about 1% to 20%; preferably from about 3% to about 15%; optimally from about 6% to about 10% by weight of the composition.

Sterile water is the major constituent of the gelled paste. Appropriate water concentrations will range from about 60% to about 95%; preferably from about 70% to about 85%; optimally from about 70% to about 75% by weight of the total composition.

Usually the compositions will also contain a moisture regulating, viscosity controlling agent in the form of a fluid polyol. Not all types of polyols are, however, suitable for the present wound dressing. Glycerine is especially suitable as a moisture control, viscosity improving agent. This polyol retards the water absorption rate so as to render the initial formulation more stable and of increased viscosity. As a result, the dressing components assemble into a flowable paste of suitable body. Other polyols such as polyethylene glycols are normally not employed as the polyol because of limited biological compatability with the human body.

In another aspect of this invention, it has been discovered that the relative amounts of the major components must be present within critical ratios. Thus, the ratio of polyacrylamide (or polymethacrylamide) to polyacrylic (or Polymethacrylic) acid salt will range from about 1:2.5 to 1:10; preferably from about 1:4 to 1:10; optimally about 1:8.

There is also a critical ratio between the amount of water and the combined amounts of polyacrylamide (or polymethacrulamide) and polyacrylic (or polymethacrylic) acid salt. Broadly the critical ratio ranges from 10:1 to 1:3. There is also a critical ratio between the amount of water and glycerine. For these two components the critical ratio varies from about 5:1 to 1:0.7, respectively; preferably about 2:1 to 1:1.

Compositions containing glycerine will incorporate this component in amounts from about 2% to 50% by weight; preferably from about 10% to 30%; optimally from about 15% to 25%.

Earlier it was mentioned that the gelled paste must have a substantially rigid character; the paste must not be easily flowable. A suitable viscosity for the water solution will range from about 10,000 to 100,000 centipoise when measured at the level of 2.5% into water by a Brookfield viscometer (spindle 3, 6 rpm) at 25° C.

Application of the aforedescribed compositions to a wound is preceded by wound preparation. First there is a debridement of necrotic tissue, a cleansing and, where necessary, application of a topical antiseptic. Thereupon, the gelled paste is applied in a layer 0.05 cm thick (minimum) or until the wound cavity is filled. If desired, the granulant can be loosely covered with a dry dressing. Sufficient room must, however, be left for expansion as exudate and contaminants are absorbed. Dressing changes should be carried out once or twice daily. Where there is more heavily contaminated or exuding wounds, more frequent changes may be necessary. When the overlaying dressing is removed, some of the gelled paste will cling thereto. Any residue is best removed by gentle irrigation of the wound with a saline. Gentle swabbing of the wound with saline will remove any granulate residue. This prepares the wound for a fresh application of the gelled paste.

The following examples will more fully illustrate various embodiments of the present invention, all parts and percentages therein being by weight, unless otherwise noted.

EXAMPLE I

A typical formulation is outlined in the table below.

TABLE I

| Component | Composition Parts by Weight |
|---|---|
| Gelamide 250 | 1 |
| Glycerine | 20 |
| Water-Lock J-550 | 8 |
| Sterile Water | 72 |

A Hobart or planetary mixer is used for stirring the components listed in the Table. Gelamide 250 is added slowly to the glycerine while mixing. Water is then added. Initially, room temperature water is used but then the remaining major portion of water should be added at 60° C. The hot water enhances the dissolving of the gelamide. Mixing is then continued until a smooth homogeneous composition is attained. This composition is cooled to room temperature. Water-Lock J-550 is then combined with the other components, care being taken to minimize mixing. There results a product which is a flowable paste whose consistency is similar to that of toothpaste. Thereafter, the gelled paste is packaged in laminated toothpaste-type tubes.

EXAMPLE II

This Example illustrates a series of formulations within the present invention. These formulations are presented to show the acceptable ranges for the ratio of polyacrylamide to polyacrylic acid. Furthermore, Table II illustrates the acceptable range of ratios for the amount of water relative to the combined sum of polyacrylamide and polyacrylic acid.

TABLE II

| ACCEPTABLE FORMULATIONS | | | | | | |
|---|---|---|---|---|---|---|
| | Experiment Number | | | | | |
| | 1 | 2 | 3 | 4 | 5 | 6 |
| Component | | | | | | |
| A. Polyacrylamide (%) | 2.6 | 7 | 2 | 4.3 | 1.5 | 1.6 |
| B. Polyacrylic Acid (%) (cross-linked) | 6.5 | 18 | 13 | 20 | 8.5 | 23 |
| C. Water (%) | 91 | 75 | 85 | 75 | 91 | 75 |
| Ratio | | | | | | |
| A:B | 1:2.5 | 1:2.5 | 1:7 | 1:5 | 1:6 | 1:14 |
| C:(A + B) | 10:1 | 3:1 | 6:1 | 3:1 | 9:1 | 3:1 |

| Experiment No. | Physical Properties of Gel |
|---|---|
| 1 | Somewhat weak, but usable, soft. |
| 2 | Good gel, difficult to extrude from the tube. |
| 3 | Good gel, exudes easily, but "grainy" (can feel the little beads). |
| 4 | Good gel, exudes well and is thixotropic (stays in wound, and adheres to skin). |
| 5 | Adequate gel, somewhat "runny" (i.e. flows |

TABLE II-continued

| | |
|---|---|
| | slightly). |
| 6 | Adequate gel, somewhat "grainy". Becomes hard to squeeze. |

TABLE III

UNACCEPTABLE FORMULATIONS

| | Experiment Number | | |
|---|---|---|---|
| | 7 | 8 | 9 |
| Component | | | |
| A. Polyacrylamide (%) | 1 | 2 | 10 |
| B. Polyacrylic Acid (%) (cross-linked) | 5 | 23 | 10 |
| C. Water | 94 | 75 | 80 |
| Ratio | | | |
| A:B | 1:5 | 1:12 | 1:1 |
| C: A + B) | 16:1 | 3:1 | 4:1 |

| Experiment No. | Physical Properties of Gel |
|---|---|
| 7 | Very watery; does not stay in tube; or on surface. |
| 8 | Very poor; does not flow at all; cheesy; granular. |
| 9 | Very poor; could not mix in polyacrylamide. |

Experiment 7 demonstrates that when the ratio of water to the sum of polyacrylamide and polyacrylic acid is greater than 10? 1, an unacceptable highly watery material is produced. Example 8 demonstrates a situation wherein the ratio of polyacrylamide to polyacrylic acid is greater than 1? 10. The product resulting from this formulation is also unacceptable because it does not flow at all, having a cheesy or granular appearance. Example 9 demonstrates that a ration of 1:1 of polyacrylamide to polyacrylic acid is totally unworkable to achieve a paste of the present invention.

EXAMPLE III

This example illustrates the ineffectiveness of a cross-linked polyacrylamide for use in the present invention. This material was made as a 4% solution in distilled water by polymerizing 99 parts acrylamide monomer with 1 part methylene bisacrylamide (cross-linking agent) with a catalyst system (potassium bisulfite, sodium bisulfite and triethyl amine). All of the aforementioned components were mixed, adding the triethyl amine last.

The resultant cross-linked acrylamide gel did not flow and was unextrudible through any narrow orifices as, for example, those found at the exit of a toothpaste type tube.

Various modifications and changes may be made with regard to the foregoing detailed description without departing from the spirit and scope of this invention.

What is claimed is:

1. A gelled paste composition for dressing skin wounds comprising:
   (i) a non-cross-linked, nonionic polyacrylamide or polymethacrylamide;
   (ii) a cross-linked salt of polyacrylic or polymethacrylic acid; and
   (iii) water, the ratio of (i) to (ii) ranging from about 1:2.5 to 1:10 and the ratio of (iii) to the sum of (i) plus (ii) ranging from about 10:1 to 1:3.

2. A composition according to claim 1 wherein there is further present an amount of glycerine, the ratio of water to glycerine being from about 5:1 to 1:0.7.

3. A composition according to claim 2 wherein the ratio of water to glycerine ranges from about 2:1 to 1:1.

4. A composition according to claim 1 wherein the ratio of (i) to (ii) ranges from about 1:4 to 1:10.

5. A composition according to claim 1 wherein the ratio of (i) to (ii) is about 1:8.

6. A composition according to claim 1 wherein the non-cross-linked nonionic polyacrylamide or polymethacrylamide is present in an amount from about 0.5 to 20% by weight.

7. A composition according to claim 1 wherein the non-cross-linked, nonionic polyacrylamide or polymethacrylamide is present in an amount from about 0.5 to 10% by weight.

8. A composition according to claim 1 wherein the non-cross-linked, nonionic polyacrylamide or polymethacrylamide is present in an amount from about 0.8 to about 2% by weight.

9. A composition according to claim 1 wherein the cross-linked salt of polyacrylic or polymethacrylic acid is present in an amount from about 1% to about 20% by weight.

10. A composition according to claim 1 wherein the cross-linked salt of polyacrylic or polymethacrylic acid is present in an amount from about 3% to about 15% by weight.

11. A composition according to claim 1 wherein the cross-linked salt of polyacrylic or polymethacrylic acid is present in an amount from about 6% to about 10% by weight.

12. A composition according to claim 1 wherein the parts (i) and (iii) have a viscosity ranging from about 10,000 to 100,000 centipoise when measured in water at 2.5% concentration using a Brookfield viscometer at 25° C.

13. A composition according to claim 1 wherein the polyacrylamide or polymethacrylamide has a molecular weight ranging from about one to ten million.

14. A composition according to claim 1 wherein the polyacrylamide or polymethacrylamide has a molecular weight ranging from about five to eight million.

* * * * *